United States Patent [19]
Freeland et al.

[11] Patent Number: 6,010,490
[45] Date of Patent: Jan. 4, 2000

[54] ABSORBENT ARTICLE HAVING AN UPSTANDING TRANSVERSE PARTITION

[75] Inventors: Mary Elaine Freeland, Loveland; Jerry Layne Dragoo, Fairfield; Patrick Jay Allen, Cincinnati, all of Ohio

[73] Assignee: The Procter & Gamble Company, Cincinnati, Ohio

[21] Appl. No.: 07/993,198

[22] Filed: Dec. 18, 1992

[51] Int. Cl.⁷ .................................................. A61F 13/15
[52] U.S. Cl. ...................... 604/385.1; 604/385.2
[58] Field of Search ...................... 604/346–348, 604/355–358, 369, 374, 375, 385.1, 385.2, 397–399, 317, 327–331, 349–354; 128/98.1; 602/67

[56] References Cited

U.S. PATENT DOCUMENTS

| | | |
|---|---|---|
| 719,811 | 2/1903 | Kent . |
| 810,689 | 1/1906 | Way . |
| 2,538,758 | 1/1951 | Bricmont . |
| 2,625,160 | 1/1953 | Maxim . |
| 2,829,647 | 4/1958 | Dexter .................................. 604/385.1 |
| 2,920,625 | 1/1960 | Green . |
| 3,522,808 | 8/1970 | Worcester . |
| 3,532,093 | 10/1970 | Lovret . |
| 3,572,342 | 3/1971 | Lindquist et al. ....................... 604/369 |
| 3,577,989 | 5/1971 | Anderson . |
| 3,626,943 | 12/1971 | Worcester . |
| 3,658,063 | 4/1972 | Schaar ................................... 604/385.1 |
| 3,774,610 | 11/1973 | Eckert et al. ......................... 604/385.1 |
| 3,776,233 | 12/1973 | Schaar ................................... 604/385.1 |
| 3,794,033 | 2/1974 | Ryan ..................................... 604/385.1 |
| 3,816,227 | 6/1974 | Schaar ................................... 604/369 |
| 3,848,595 | 11/1974 | Endres ................................... 604/385.1 |
| 3,848,599 | 11/1974 | Schaar ................................... 604/385.1 |
| 3,884,234 | 5/1975 | Taylor ................................... 604/385.1 |
| 3,885,568 | 5/1975 | Schaar ................................... 604/378 |
| 3,926,189 | 12/1975 | Taylor ................................... 604/397 |
| 4,029,100 | 6/1977 | Karami ................................... 604/374 |
| 4,100,922 | 7/1978 | Hernandez ........................... 604/385.1 |
| 4,662,877 | 5/1987 | Williams . |
| 4,695,278 | 9/1987 | Lawson ................................. 604/385.2 |
| 4,781,713 | 11/1988 | Welch et al. ......................... 604/385.1 |
| 4,892,536 | 1/1990 | DesMarais et al. ................. 604/385.2 |
| 4,895,568 | 1/1990 | Enloe ................................... 604/385.2 |
| 4,950,263 | 8/1990 | Lewis ................................... 604/385.1 |
| 4,968,312 | 11/1990 | Khan ................................... 604/385.1 |
| 4,990,147 | 2/1991 | Freeland ............................... 604/385.2 |
| 5,037,413 | 8/1991 | Haque ................................... 604/385.2 |
| 5,062,840 | 11/1991 | Holt et al. ........................... 604/385.1 |

FOREIGN PATENT DOCUMENTS

| | | | |
|---|---|---|---|
| 2495899 | 6/1982 | France ................................... 604/354 |
| 2561078 | 9/1985 | France . |
| 2573629 | 5/1986 | France . |
| 27 31 969 | 5/1979 | Germany . |
| 28 03 500 | 8/1979 | Germany . |
| 3038192 | 12/1982 | Germany ............................... 604/385 |
| 3186262 | 8/1991 | Japan ................................... 604/385.2 |
| 5202057 | 9/1991 | Japan ................................... 604/385.2 |
| 2022026 | 11/1991 | Spain . |

*Primary Examiner*—John G. Weiss
*Assistant Examiner*—K. M. Reichle
*Attorney, Agent, or Firm*—Larry L. Huston; E. Kelly Linman; Jacobus C. Rasser

[57] ABSTRACT

A disposable absorbent article having a transverse partition. The transverse partition is upstanding from the topsheet and presents an abrupt discontinuity out of the plane of the disposable absorbent article and obstructs fecal material deposited in the rear portion of the disposable absorbent article from migrating to the front portion of the disposable absorbent article. This obstruction minimizes soiling of the genitalia of the wearer. The disposable absorbent article may have upstanding barrier leg cuffs. The transverse partition may connect the barrier leg cuffs to form an H-shape.

17 Claims, 2 Drawing Sheets

ABSORBENT ARTICLE HAVING AN UPSTANDING TRANSVERSE PARTITION

FIELD OF THE INVENTION

The present invention relates to disposable absorbent articles, and more particularly to disposable absorbent articles which minimize the migration of fecal material deposited thereon.

BACKGROUND OF THE INVENTION

Disposable absorbent articles, such as diapers, are well known in the art. Disposable absorbent articles retain and absorb body exudates, such as urine and fecal material deposited thereon.

Significant advances have been made in the art relative to absorbing and retaining urine deposits. For example, disposable absorbent articles seldom leak and may be relatively thin due to the incorporation of absorbent gelling materials.

However, fewer attempts have been made in the art to handle deposits of fecal material in disposable absorbent articles. Fecal material has the undesirable proclivities of smearing onto the wearer's skin, causing epidermal irritation and complicating the task of cleaning the wearer when the soiled diaper or other disposable absorbent article is removed.

To overcome these proclivities, certain attempts have been made in the art to isolate the fecal material from the skin of the wearer. Such attempts generally provide a void or hole into which the fecal material is deposited and retained (hopefully), so that the location of the fecal material is limited to the position of the void or hole. Examples of such attempts are found in U.S. Pat. No. 4,662,877 issued May 5, 1987, to Williams; U.S. Pat. No. 4,892,536 issued Jan. 9, 1990, to DesMarais et al.; U.S. Pat. No. 4,968,312 issued Nov. 6, 1990, to Khan; U.S. Pat. No. 4,990,147 issued Feb. 5, 1991, to Freeland; U.S. Pat. No. 5,062,840 issued Nov. 5, 1991, to Holt et al.

Other attempts have been made in the art to provide cups which attempt to circumscribe the anal opening, the genitalia, or both in an attempt to isolate these regions of the wearer's body. These attempts can be uncomfortable for the wearer and require precise positioning of the cup.

In still another attempt, resilient barriers extending transversely or longitudinally have been placed below the topsheet of the diaper. But this arrangement suffers from the drawback that fecal material deposited on the topsheet is above the barrier, can still migrate and still cause the aforementioned problems. This arrangement simply does not provide the abrupt discontinuity necessary to obstruct migration of fecal material deposited on the topsheet of the diaper.

Furthermore, such an arrangement may even be ineffective in preventing excessive transverse migration of the fecal material. A barrier disposed below the topsheet cannot be easily joined to longitudinally extending barrier leg cuffs, which, as are well known in the art, minimize leakage from the diaper. Thus, fecal material which is channeled towards transverse migration by the barrier may be transported to the perimeter of the diaper and breach the perimeter, causing leakage.

Accordingly, it is an object of this invention to provide a disposable absorbent article having a transverse barrier which may be used in conjunction with other components of the disposable absorbent article, such as barrier leg cuffs, to minimize leakage. It is further an object of this invention to provide a disposable absorbent article which limits the migration of fecal material, thereby reducing epidermal contact with the fecal material and minimizing cleaning by the caretaker. Finally, it is an object of this invention to provide an abrupt surface discontinuity in a disposable absorbent article to obstruct the flow of fecal material in the longitudinal direction.

BRIEF DESCRIPTION OF THE DRAWINGS

While the Specification concludes with claims particularly pointing out and distinctly claiming the present invention, it is believed the same will be better understood from the following description taken in conjunction with the associated drawings in which like reference numerals represent the same component and:

BRIEF SUMMARY OF THE INVENTION

The present invention comprises a disposable absorbent article, such as a diaper. The disposable absorbent article has a liquid pervious topsheet with an outwardly oriented body facing surface which is oriented towards the wearer while in use and a core facing surface opposed to the body facing surface. The disposable absorbent article further comprises a liquid impervious backsheet at least partially peripherally joined to the topsheet and an absorbent core intermediate the topsheet and the backsheet.

The disposable absorbent article further comprises a transverse partition disposed on the body facing surface of the topsheet and extending outwardly therefrom, to be upstanding and extend away from the plane of the disposable absorbent article. The transverse partition divides the disposable absorbent article into a front portion and a rear portion, and presents an abrupt discontinuity between the front portion and the rear portion. Fecal material deposited in the rear portion of the disposable absorbent article is obstructed from longitudinally migrating to the front portion of the disposable absorbent article by the transverse partition.

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants or incontinent persons about the lower torso of the wearer. It should be understood, however, that the present invention is also applicable to other absorbent articles such as incontinent briefs, incontinent undergarments, diaper holders and liners, certain feminine hygiene garments, and the like.

Figure 1:
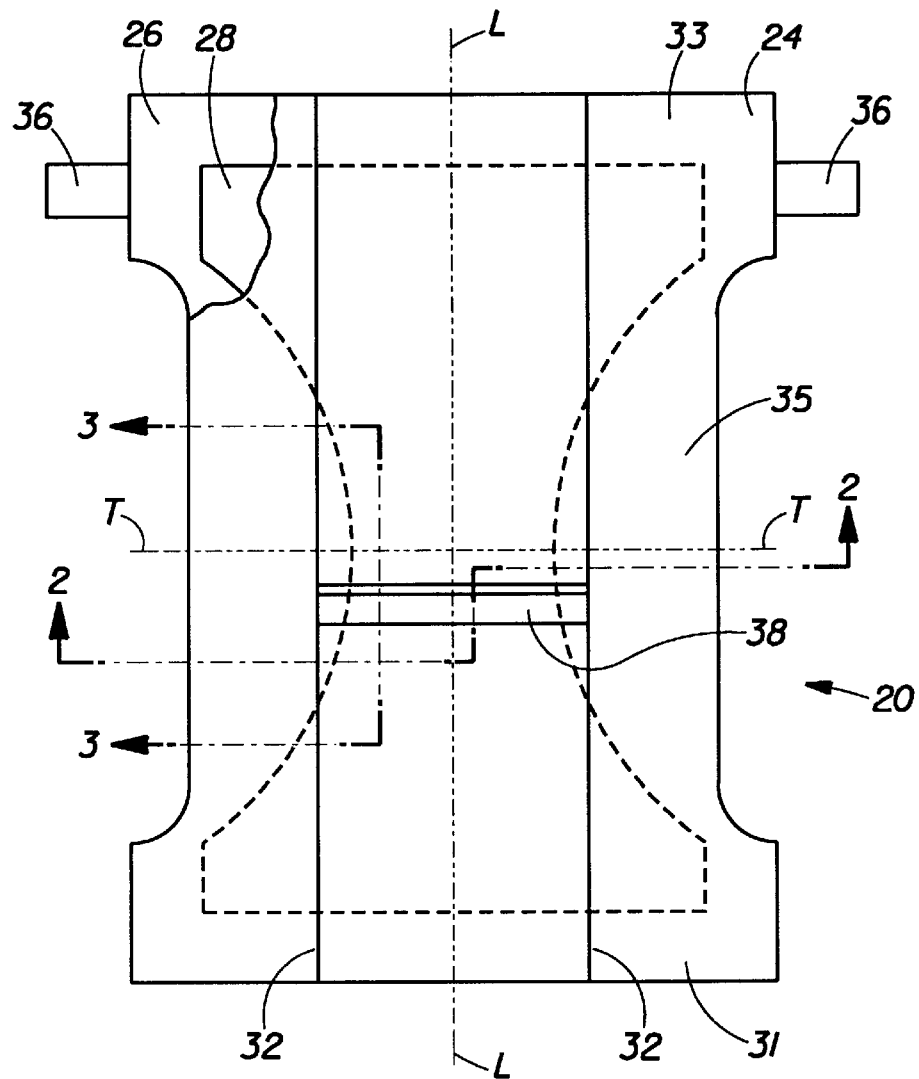
FIG. 1 is a top plan view of a disposable absorbent article according to the present invention, shown partially in cutaway, and having the foam cap omitted for clarity and having no elastic induced contraction.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces or contacts the wearer, the inner surface, oriented towards the viewer. As shown in FIG. 1, the diaper 20 preferably comprises a liquid pervious topsheet 24; a liquid impervious backsheet 26 joined with the topsheet 24; an absorbent core 28 positioned between the topsheet 24 and the backsheet 26; elasticized barrier leg cuffs 32; a fastening system generally multiply designated as 36; and an upstanding transverse partition 38.

The topsheet 24 of the diaper 20 has an outwardly oriented body facing surface which faces (and usually contacts) the wearer while the diaper 20 is in use and a core facing surface opposed to the body facing surface. The body facing surface of the topsheet 24 of the diaper 20 comprises that portion of the diaper 20 which is positioned adjacent the wearer's body during use (i.e., the inner surface generally is formed by both at least a portion of the topsheet 24 and other components joined to the topsheet 24). The diaper 20 further has a first waist region 31 oriented towards the front of the wearer while the diaper is in use, a second waist region 33 longitudinally opposite the first waist region 31, a crotch region 35 positioned between the first waist region 31 and the second waist region 33, and a periphery which is defined by the outer edges of the diaper 20.

The diaper 20 has a longitudinal axis L—L which divides the diaper 20 into left and right halves, and which divides the standing wearer into left and right body halves. The diaper 20 further comprises a transverse axis T—T orthogonal to the longitudinal axis L—L which divides the diaper 20 into a front portion and a rear portion. Orthogonal to the mutually perpendicular longitudinal axis L—L and transverse axis T—T, is a Z-direction axis, which extends outwardly from the plane of the diaper 20.

A component of the diaper 20 is considered to be transversely oriented, and hence "transverse" if such component forms an angle of ±45 degrees or less with the transverse centerline T—T. Similarly, a component is considered to be longitudinally oriented, and hence "longitudinal" if such component forms an angle of ±45 degrees or less with the longitudinal axis L—L.

FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, preferred diaper configurations are described generally in U.S. Pat. No. 3,860,003, entitled "Contractable Side Portions for Disposable Diaper" which issued to Kenneth B. Buell on Jan. 14, 1975; and U.S. patent application Ser. No. 07/715,152, allowed, "Absorbent Article With Dynamic Elastic Waist Feature Having A Predisposed Resilient Flexural Hinge", Kenneth B. Buell et al. filed Jun. 13, 1991; each of which is incorporated herein by reference.

The absorbent core 28 may be any absorbent means which is generally compressible, conformable, non-irritating to the wearer's skin, and capable of absorbing and retaining liquids such as urine and other certain body exudates. As shown in FIG. 1, the absorbent core 28 has a garment surface, a body surface, side edges, and waist edges. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults. Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference.

The backsheet 26 is positioned adjacent the garment surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and are marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). Particularly preferred materials for the backsheet 26 include RR8220 blown films and RR5475 cast films as manufactured by Tredegar Industries, Inc. of Terre Haute, Ind. The backsheet 26 is preferably embossed and/or matte finished to provide a more clothlike appearance. Further, the backsheet 26 may permit vapors to escape from the absorbent core 28 (i.e., breathable) while still preventing exudates from passing through the backsheet 26.

The topsheet 24 is positioned adjacent the body surface of the absorbent core 28 and is preferably at least partially peripherally joined thereto and to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 24 and the backsheet 26 are joined directly to each other in the diaper periphery and are indirectly joined together as a result of their joinder to the absorbent core 28 by suitable attachment means (not shown).

The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids contained in the absorbent core 28. There are a number of manufacturing techniques which may be used to manufacture the topsheet 24. For example, the topsheet 24 may be a nonwoven web of fibers spun-bonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

The diaper 20 preferably further comprises elasticized barrier leg cuffs 32 for providing improved containment of liquids and other body exudates. Each elasticized barrier leg cuff 32 may comprise several different embodiments for reducing the leakage of body exudates from the leg regions of the diaper 20. U.S. Pat. No. 4,909,803 entitled "Disposable Absorbent Article Having Elasticized Flaps" issued to Aziz et al. on Mar. 20, 1990, describes a disposable diaper 20 having "stand-up" elasticized flaps (barrier leg cuffs 32) to improve the containment of the leg regions of the diaper 20. U.S. Pat. No. 4,695,278 entitled "Absorbent Article Having Dual Cuffs" issued to Lawson on Sep. 22, 1987, describes a disposable diaper 20 having dual cuffs including both a gasketing cuff and a barrier cuff 32. Both of these patents are incorporated herein by reference for the purpose of showing suitable exemplary constructions for the barrier leg cuffs 32.

Spanning the transverse distance between the barrier leg cuffs 32 is an upstanding transverse partition 38. The transverse partition 38 is disposed on the body facing surface of the topsheet 24 and extending outwardly therefrom to present an abrupt discontinuity in the body facing surface of the topsheet 24. The transverse partition 38 obstructs the longitudinal migration of fecal material deposited in the rear portion of the diaper 20 towards the front portion of the diaper 20. Preferably the upstanding partition 38 connects the barrier leg cuffs 32, forming an H-shape. As illustrated, preferably the transverse partition 38 is generally straight, rectilinear, transverse and preferably parallel to the transverse axis T—T of the diaper 20. If desired, the transverse pattern 38 may even be coincident with the transverse axis T—T of the diaper 20.

Figure 2:
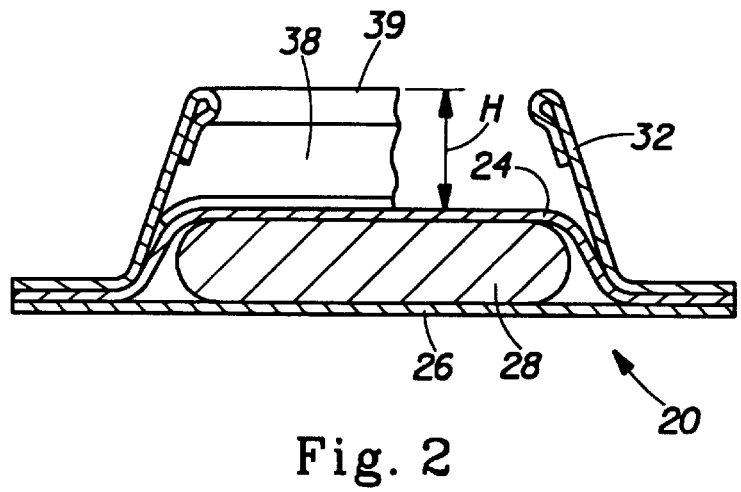
FIG. 2 is an offset vertical sectional view taken along line 2—2 of FIG. 1.

Referring to FIG. 2, the transverse partition 38 has a proximal edge which is preferably joined to the topsheet 24, and particularly the body facing surface thereof, by adhesive or other joining means, as are well known in the art. The transverse partition 38 extends outwardly from the plane of the topsheet 24 with a vector component in the Z-direction to a distal edge.

It is important the transverse partition 38 be upstanding and rise above the plane of the topsheet 24 to an effective height H sufficient to present an abrupt discontinuity to obstruct the longitudinal movement of fecal material while the diaper 20 is worn. It is to be recognized that if the topsheet 24 has wrinkles, rugosities, undulations, or other deviations from planarity, these should be taken into account at the position of the transverse partition 38 when determining its effective height H. Otherwise such deviations from planarity in the topsheet 24 may diminish the effective height H of the distal edge of the partition 38 above the topsheet 24, and not sufficiently obstruct the flow of fecal material.

As used herein, the "effective height" is the Z-direction distance from the proximal edge of the transverse partition 38 to the distal edge of the transverse partition 38. The transverse partition 38 preferably has an effective height H above the body facing surface of the topsheet 24 of at least 1.5 centimeters, more preferably 2.5 centimeters, and most preferably at least about 3.5 centimeters.

Figure 3:
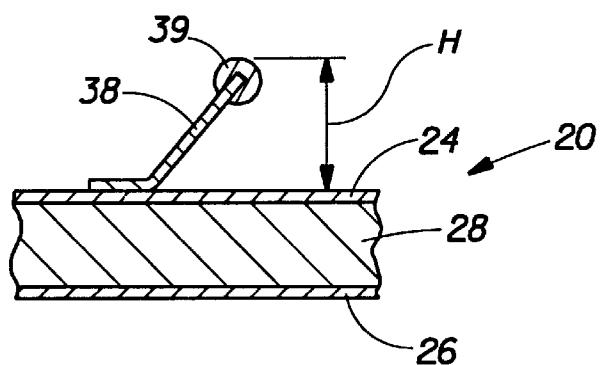
FIG. 3 is a fragmentary instant vertical sectional view taken along line 3—3 of FIG. 1.

As illustrated in FIG. 3, the transverse partition 38 is preferably not orthogonal to the plane of the topsheet 24, but instead is disposed in angular relationship therewith so that the distal end of the upstanding transverse partition 38 is oriented towards the rear portion and the rear waist margin 33 of the diaper 20. This arrangement provides the advantage that the pressure of the fecal material helps seal the transverse partition 38 against the wearer's body, minimizing the leakage of fecal material across the transverse partition 38. This arrangement further minimizes the vertical forces necessary to maintain the transverse partition 38 in contact with the body of the wearer.

The transverse partition 38 may be made of a water pervious material, but is preferably made of a water impervious material, the water impervious material prevents (or minimizes the amount of) runny fecal material from reaching the genitalia of the wearer. Nonwoven materials, such as may be used to form the barrier leg cuffs 32, have been found to be particularly suitable in the transverse partition 38. Other suitable materials for the transverse partition 38 include foams, formed films, etc. If desired, small discrete stryofoam beads may be placed in a water impervious casing to form the transverse partition 38. This arrangement provides a partition which conforms to the groove between the legs of the wearer, particularly the female wearer, and allows the transverse partition to fit into such groove. Such fitting of the transverse partition 38 to the groove of the wearer (which is typically a continuation of the gluteal groove) minimizes the flow channel beyond the transverse partition 38 through which fecal material may be transported to the front portion of the diaper 20.

If desired, a transverse linear elastic strand may be applied to the distal edge of the transverse partition 38 to provide transverse contraction. Alternatively, a foam cap 39 may be applied to the distal edge of the transverse partition 38 to increase wearer comfort. The foam cap 39 may be elastically extensible in the transverse direction, as illustrated.

Figure 4:
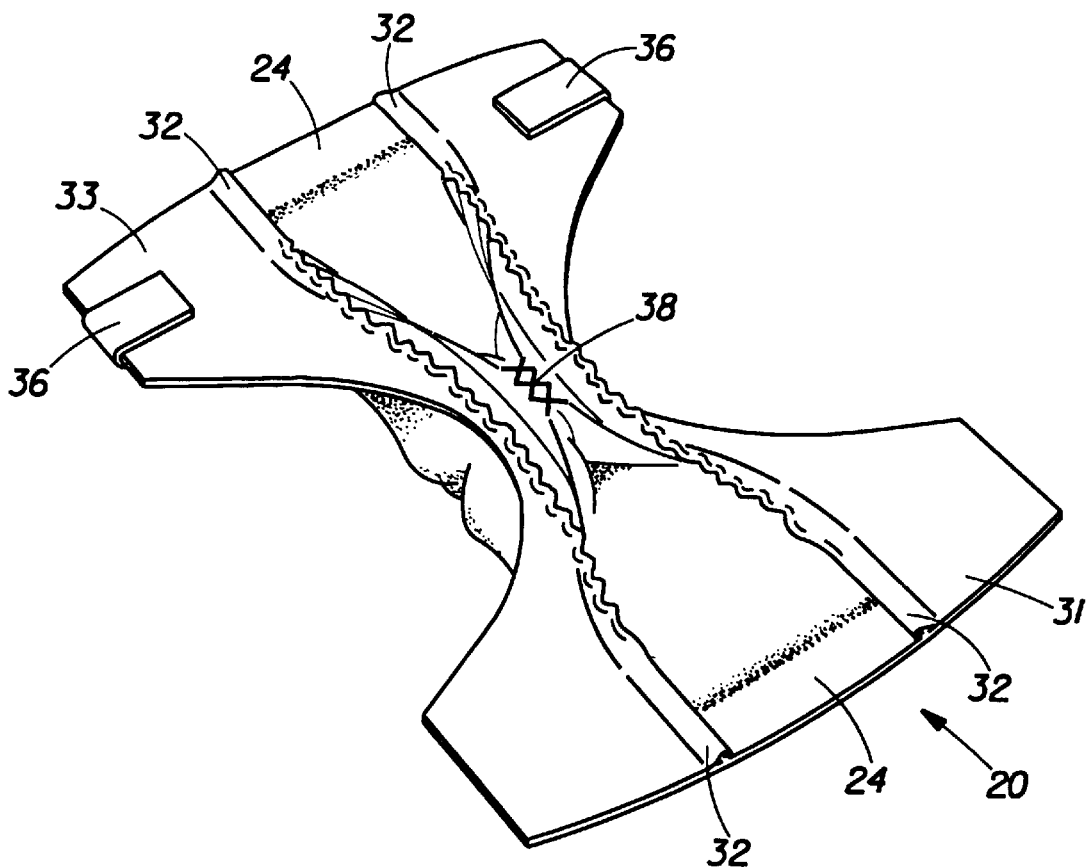
FIG. 4 is a perspective view of an alternative embodiment of a diaper according to the present invention having the transverse partition formed by joining the barrier leg cuffs together.

In contrast to the embodiment of FIGS. 1–2 which has an elastically extensible transverse partition 38, and hence imparts very little transverse deformation to the barrier leg cuffs 32, the transverse partition 38 may be generally inelastic and transversely foreshorten the crotch region 35 of the diaper 20, as illustrated by FIG. 4. Such a transverse partition 38 may be formed by joining the sides of the diaper 20, particularly the barrier leg cuffs 32, together, so that the crotch region 35 of the diaper 20 is upstanding from the plane of the topsheet 24 to present the abrupt discontinuity. This arrangement provides advantages that wearer comfort is enhanced by having a relatively narrow crotch region 35 and a separate component is not necessary to form the transverse partition 38.

Furthermore, due to rugosities formed by foreshortening the core 28, some fecal material may leak into the front portion of the diaper 20, i.e., such rugosities act as a safety valve to prevent the fecal material from leaking out the rear waist margin. If one desires to reduce these rugosities, the topsheet 24 should not be joined to the core 28, so that the topsheet 24 may be interposed between the barrier leg cuffs 32 upon joining.

It will be obvious to one skilled in the art that other variations and arrangements are feasible and within the scope of the claimed invention. For example, the transverse partition 38 need not necessarily be rectilinear, but may be curvilinear. Generally if a curvilinear transverse partition 38 is selected, it should be concave towards the rear portion 33 of the diaper 20. Elastic strands may be applied to the transverse partition 38 in the vertical direction or in a fan-shaped arrangement radiating outwardly from the center of the proximal edge of the transverse partition 38. The transverse partition 38 may have small gaps juxtaposed with the barrier leg cuffs 32, to allow flow of fecal material from the rear portion of the diaper 20 to the front portion of the diaper 20 in the event of heavy loading between diaper 20 changes. Such gaps provide a safety valve to prevent the fecal material from breaching the perimeter of the diaper 20. All such variations are within the scope of the appended claims.

The diaper 20 is preferably applied to a wearer by positioning one of the waist regions 31 or 33, preferably the second waist region 33 (which typically has the fastening system 36), under the wearer's back and drawing the remainder of the diaper 20 between the wearer's legs so that the other waist region 31, preferably the first waist region 31, is positioned across the front of the wearer. The tape tabs of the fastening system are then released from the release portion. The diaperer then wraps the elasticized side panel around the wearer, while still grasping the tab portion. The elasticized side panels will typically be extended and tensioned during this operation so as to conform to the size and shape of the wearer. The fastening system 36 is secured to the outer surface of the diaper 20 to effect a side closure.

What is claimed is:

1. A disposable absorbent article having a longitudinal axis and a transverse axis orthogonal thereto, said disposable absorbent article comprising:

a liquid pervious topsheet having an outwardly oriented body facing surface and a core facing surface opposed thereto;

a liquid impervious backsheet at least partially peripherally joined to said topsheet;

an absorbent core intermediate said topsheet and said backsheet;

two longitudinal barrier leg cuffs upstanding from said outwardly oriented body facing surface of said topsheet;

a transverse partition formed by directly affixing said barrier leg cuffs together without an intermediate member therebetween, said transverse partition dividing said disposable absorbent article into a front portion and a rear portion whereby fecal material deposited in said rear portion of said disposable absorbent article is obstructed from migrating to said front portion of said disposable absorbent article.

2. A disposable absorbent article according to claim 1 wherein said transverse partition is substantially transversely inelastic.

3. A disposable absorbent article according to claim 2 wherein said disposable absorbent article has a first waist region, a second waist region, and a crotch region therebetween, said transverse partition transversely foreshortening the crotch region of said disposable absorbent article.

4. A disposable absorbent article according to claim 3 wherein said transverse partition has an effective height of at least 1.5 centimeters.

5. A disposable absorbent article according to claim 4 wherein said transverse partition has an effective height of at least 3.5 centimeters.

6. A disposable absorbent article according to claim 1 wherein said transverse partition has a proximal edge joined to said topsheet and extends outwardly therefrom to a distal edge, said distal edge being angled towards said rear portion of said disposable absorbent article relative to said proximal edge.

7. A disposable absorbent article having a longitudinal axis and a transverse axis orthogonal thereto, said disposable absorbent article comprising:

a liquid pervious topsheet having an outwardly oriented body facing surface and a core facing surface opposed thereto;

a liquid impervious backsheet at least partially peripherally joined to said topsheet;

an absorbent core intermediate said topsheet and said backsheet; and a compliant, substantially inelastic transverse partition disposed on said body facing surface of said topsheet and extending from said topsheet, said transverse partition dividing said disposable absorbent article into a front portion and a rear portion, whereby fecal material deposited in the rear portion of said disposable absorbent article is obstructed from migrating to the front portion of said disposable absorbent article.

8. A disposable absorbent article according to claim 1 wherein said transverse partition is substantially liquid impervious.

9. A disposable absorbent article according to claim 8 wherein said transverse partition has a proximal edge joined to said topsheet and extends outwardly therefrom to a distal edge, said disposable absorbent article further comprising a foam cap on said distal edge of said transverse partition.

10. A disposable absorbent article according to claim 1 having a front waistband, a rear waistband, and a crotch portion intermediate said front waistband and said rear waistband, wherein said transverse partition transversely foreshortens said crotch portion of said disposable absorbent article.

11. A disposable absorbent article according to claim 7 wherein said disposable absorbent article topsheet has irregularities therein.

12. A disposable absorbent article according to claim 11 wherein said transverse partition has an effective height of at least 1.5 centimeters.

13. A disposable absorbent article according to claim 12 wherein said transverse partition has an effective height of at least 3.5 centimeters.

14. A disposable absorbent article according to claim 1 wherein said transverse partition has an effective height of at least 1.5 centimeters.

15. A disposable absorbent article according to claim 14 wherein said transverse partition has an effective height of at least 3.5 centimeters.

16. A disposable absorbent article according to claim 7 wherein said transverse partition has a proximal edge joined to said topsheet and extends outwardly therefrom to a distal edge, said distal edge being angled towards said rear portion of said disposable absorbent article relative to said proximal edge.

17. A disposable absorbent article according to claim 7 wherein said compliant substantially inelastic transverse partition is substantially transversely inelastic.

* * * * *